United States Patent [19]

Verhoeven et al.

[11] Patent Number: 5,449,830
[45] Date of Patent: Sep. 12, 1995

[54] REGIOSPECIFIC PROCESSES TO MAKE CIS-1-AMINO-2-ALKANOL FROM DIOL OR HALOHYDRIN

[75] Inventors: Thomas R. Verhoeven, Cranford; Edward F. Roberts, Princeton; Chris H. Senanayake, North Brunswick; Kenneth M. Ryan, Skillman, all of N.J.

[73] Assignee: Merck & Co., Inc. Rahway, N.J.

[21] Appl. No.: 212,604

[22] Filed: Mar. 11, 1994

[51] Int. Cl.$^6$ .......................................... C07C 209/16
[52] U.S. Cl. ................................. 564/400; 564/415
[58] Field of Search ............... 564/400, 415, 447, 428

[56] References Cited

U.S. PATENT DOCUMENTS 3,534,055 10/1970 Gittos et al. ...................... 260/295
4,128,666 12/1978 Bondinell et al. ................. 424/330
5,113,025 5/1992 Park et al. ......................... 568/814

FOREIGN PATENT DOCUMENTS 0541168 5/1993 European Pat. Off. .

OTHER PUBLICATIONS

S. M. Sutter, et al. J. Am. Chem. Soc. vol. 62, p. 3473, (1940).
D. R. Dalton, et al. J. C. S. Chem. Commun. p. 591, (1966).
M. Imuta, et al. J. Org. Chem. vol. 43, p. 4540, (1978).

*Primary Examiner*—Richard L. Raymond
*Assistant Examiner*—Brian M. Burn
*Attorney, Agent, or Firm*—Roy D. Meredith; Jack L. Tribble

[57] ABSTRACT

A regioselective processes are disclosed for the synthesis of (1R,1S)-amino-(2S,2R)-alkanol, particularly (1R,1S)-amino-(2S,2R)-indanol.

6 Claims, No Drawings

REGIOSPECIFIC PROCESSES TO MAKE CIS-1-AMINO-2-ALKANOL FROM DIOL OR HALOHYDRIN

BACKGROUND OF THE INVENTION

The present application is related to Merck 18996, U.S. Ser. No. 08/059,038, filed May 7, 1993, and Merck case 19114 U.S. Ser. No. 108/212,603).

The present invention is concerned with a novel intermediate and process for synthesizing compounds which inhibit the protease encoded by human immunodeficiency virus (HIV), and in particular certain oligopeptide analogs, such as compound J of the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns a process to effect the regiospecific generation of a cis-1-amino-2-alklanol, particularly cis-1-amino-2-indanol (Compounds C and F) from either a 1,2 diol precursor or from a 2-halo-1-alkanol. For 1,2-diol precursors, the stereochemical integrity of the carbon-oxygen bond at position 2 of the indan core is retained, so that there is substantially complete conversion to the appropriate product 1-amino-2-indanol. For example, 1R,2S-indandiol and 1S,2S-indandiol (Compounds A and B) each produce substantially 1R-amino-2S-indanol (Compound C). Similarly, 1R,2R-indandiol and 1S,2R indandiol each produce substantially 1S,2R-indandiol. Mixtures of enantiomeric diol precursors produce substantially the same mixture of 1-amino-2-alkanol enantiomers.

For 2-halo-1-indanol precursors, the stereochemistry of the carbon at position 2 of the indane core is inverted so that there is substantially complete conversion to the appropriate product cis-1-amino-2-indanol. For example, 2S-bromo-1S-indanol (compound G) produces substantially 1S-amino-2R-indanol (Compound F), and 2R-bromo-1R-indanol (compound H) produces substantially 1R-amino-2S-indanol (Compound C). Mixtures of enantiomeric 2-halo-1-alkanol precursors produce substantially the same mixture of 1-amino-2-alkanol enantiomers.

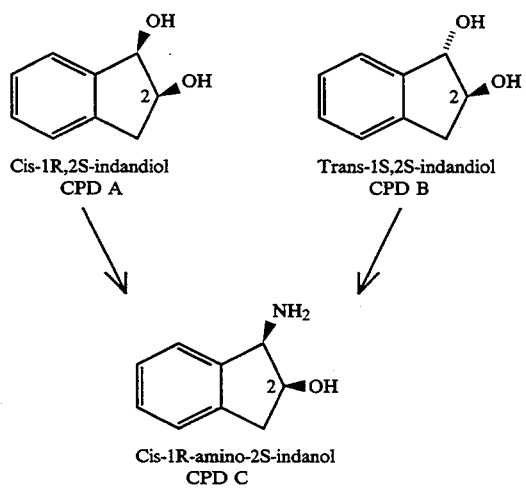

Cis-1R,2S-indandiol
CPD A

Trans-1S,2S-indandiol
CPD B

Cis-1R-amino-2S-indanol
CPD C

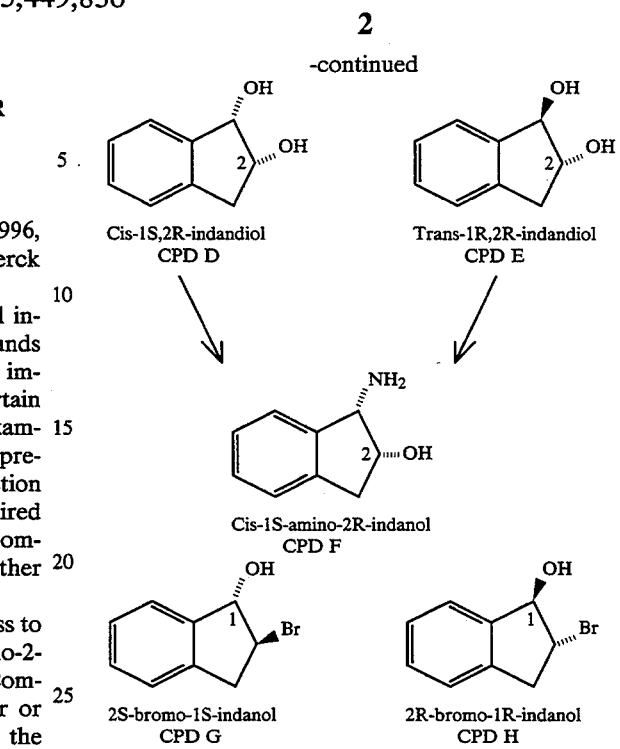

Cis-1S,2R-indandiol
CPD D

Trans-1R,2R-indandiol
CPD E

Cis-1S-amino-2R-indanol
CPD F 2S-bromo-1S-indanol
CPD G 2R-bromo-1R-indanol
CPD H The process described is superior to prior art in that the process is shorter, more productive, higher yielding and has less environmental impact.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313,277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including certain oligopeptide analogs that can be made from the novel intermediates and processes of this invention are inhibitors of HIV protease, and are disclosed in EPO 541,168, which published on May 12, 1993. See, for example, compound J therein.

Previously, the synthesis of compound J and related compounds was accomplished via a 12-step procedure. This procedure is described in EPO 541,168. The extreme length of this route (12 steps), renders this process time consuming and labor intensive, and it requires the use of many presently expensive reagents and a presently expensive starting material. A route requiting fewer reaction steps and reagents would provide desirable economical and time-saving benefits.

In the case of the diol precursor, this invention provides a process for the regiospecific synthesis of cis-1-amino-2-indanol from 1,2-indane diol, with specific retention of the stereochemical integrity of the carbon at the 2 position. The indane diol is treated with a strong acid, then hydrolyzed with water to give the target compound. This process of the present invention is a one step procedure, and avoids isolation of any intermediate.

For the 2-halo-1-indanol precursor, this invention provides a process for the regiospecific synthesis of cis-1-amino-2-indanol, with the specific inversion of the stereochemistry of the carbon at the 2 position. The 2-halo-1-indanol is treated with strong acid to give a 1-acetamido-2-halo intermediate, then base is added to form an oxazoline intermediate. Treatment with aqueous weak acid gives the desired product.

The preparation of 1-amino-2-indanol was previously accomplished via a multistep sequence. This sequence involved the treatment of an indene oxide with aqueous ammonia to produce a trans 1-amino-2-indanol (Cpd J).

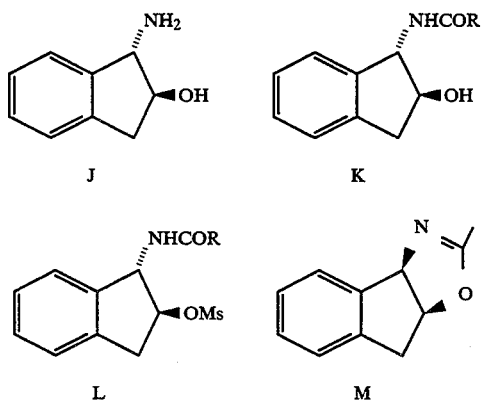

The intermediate J was then treated with an acyl halide, thereby converting the amine to an amide intermediate (Cpd K). The hydroxyl group of the hydroxy amide K is activated by conversion to a mesylate (Cpd L), then induced to cyclize and form the oxazoline M. The oxazoline B produced by this prior art method is purified, then subjected to conditions similar to that described above effecting its conversion to the target cis-1-amino-1-indanol.

The application of 1,2 diols in the Ritter reaction is novel. See, for example, L. I. Krimen et al., *Organic Reactions Vol. 17* John Wiley & Sons New York 1969 (covers up to 1966); R. Bishop, *Comprehensive Organic Synthesis* eds. B. M. Trost et al., Pergammon Press New York, 1991 vol. 6. Glycols are well known when the two alcohol functions are separated by more than one carbon atom. They react as individual alcohols or assist in forming a larger ring. Based on known chemistry in the literature, one would expect a 1,2 diol in strong acid to undergo a pinacol rearrangement to lose a mole of water and form 2-indanone, as pictured as follows.

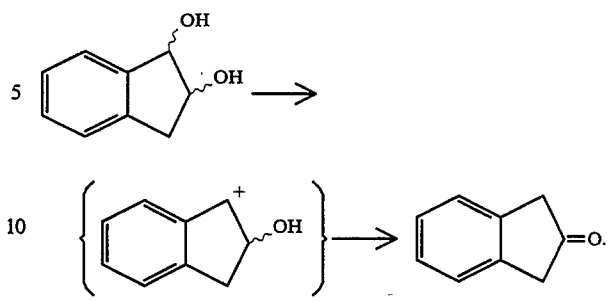

The process of the present invention provides a route with fewer chemical steps to accomplish the same overall synthesis of cis-1-amino-2-indanol. Furthermore, the isolation of intermediates is not necessary in the present invention. Also, the present process utilizes smaller quantities of organic solvents and proceeds in greater overall yield than prior methods, a result providing lower environmental impact than prior methods.

BRIEF DESCRIPTION OF THE INVENTION

The present invention provides new methods to effect the regiospecific generation of a ( 1S, 1R)-amino-(2R,2S)-alkanol, particularly 1S-amino-2R-indanol or 1R-amino-2S-indanol. Two different reactants are used, the 1,2-diol and the 2-halo-1-alkanol. The product compounds are intermediates for the synthesis of compounds useful as inhibitors of HIV protease, renin and other proteases.

DETAILED DESCRIPTION OF THE INVENTION

The present invention provides new methods for making the enantiomeric intermediates 1-amino-2-alkanol, particularly 1S-amino-2R-indanol or 1R-amino-2S-indanol. These intermediates are useful for the preparation of HIV protease inhibitors.

In a first method, the desired product is synthesized from a diol reactant, e.g., 1,2-indane diol. This first method involves retention of the stereochemical integrity of the carbon-oxygen bond at C-2 in the reactant 1,2-indane diol. In a second method, the desired product is synthesized from a 2-halo-1-alkanol reactant, e.g., 2-bromo-1-indanol. This second method involves inversion of the stereochemistry of the carbon at the 2-position of the indane core, said 2-position situated two carbons distal from the phenyl group in the fused cyclopentyl ring of the indane core.

A. DIOL REACTANT

This invention relates to a regioselective process for synthesizing any enantiomer of cis-1-amino-2-indanol, or mixture of said enantiomers, from 1,2-indane diol, said process substantially retaining the stereochemical integrity of the carbon-oxygen bond at C-2 in the 1,2-indane diol, wherein the process comprises the steps of
(a) mixing one equivalent of 1,2-indane diol in a solvent, said solvent selected from an alkyl nitrile or aryl nitrile;
(b) adding to the mixture about at least about 1.5 equivalents of an acid, said acid selected from a strong protic acid or a Lewis acid or an organic acid, and maintaining thereafter the temperature of the resulting mixture between about −70° C. and about 30° C. for a time period of between about 0.25 hours to about 6.0 hours; and (c) adding excess water to effect hydrolysis, and stirring for a time period of between about 0.5 hour and about 8.0 hours, at a temperature of between about 25° C. and about 80° C., to give substantially cis-1-amino-2-indanol.

The present invention provides a process for the synthesis of cis-1-amino-2-indanol from 1,2-indane diol. In this particular application, 1,2-indane diol is readily synthesized by a variety of methods, both in racemic and optically pure form. The starting material, in any mixture of enantiomers including racemic and optically pure forms, is treated with a strong protic acid, such as sulfuric acid or $H_2SO_{4-}SO_3$, or Lewis acid such as boron trifluoride, or an organic acid such as p-toluenesulfonic acid, methanesulfonic acid, trifluoroacetic acid or trifluoromethanesulfonic acid. The reaction is carried out in a solvent comprising alkyl or aryl nitrile, e.g., acetonitrile, proprionitrile, or benzonitrile, at a temperature range of between about −70° C. to about +30° C., and an incubation period ranging from about 0.25 to about 6.0 hours. Isolation of the final product is accomplished by treatment with water for a period of 0.5 to 8 h at a temperature of 25°–80° C. This effects hydrolysis of the intermediate(s) and produces the cis-1-amino-2-indanol. Isolation of the final product as either its crystalline free base (i.e. amino-indanol) or as an amine salt derivative (e.g. a tartaric acid salt) can be accomplished directly from the reaction medium by pH adjustment to provide the desired form of the amino indanol intermediate.

One embodiment is a regioselective process, for synthesizing 1R-amino-2S-indanol from reactant (1R,2S)-indandiol or reactant (1S,2S)-indandiol or mixture of said reactants, said process substantially retaining the stereochemical integrity of the carbon-oxygen bond at C-2 in the 1,2-indandiol, wherein the process comprises the steps of
(a) mixing in a solvent one equivalent of reactant, said reactant selected from ( 1R,2S)-indandiol or ( 1S,2S)-indandiol or mixture thereof, said solvent selected from an alkyl nitrile or aryl nitrile;
(b) adding to the mixture about two equivalents of an acid, said acid selected from a strong protic acid or a Lewis acid or an organic acid, and maintaining thereafter the temperature of the resulting mixture between about −70° C. and about 30° C. for a time period of between about 0.25 hours to about 6.0 hours; and
(c) adding excess water to effect hydrolysis, and stirring for a time period of between about 0.5 hour and about 8.0 hours, at a temperature of between about 25° C. and about 80° C., to give 1R-amino-2S-indanol.

Another embodiment is a regioselective process, for synthesizing 1S-amino-2R-indanol from reactant (1S,2R)-indandiol or reactant (1R,2R)-indandiol or mixture of said reactants, said process substantially retaining the stereochemical integrity of the carbon-oxygen bond at C-2 in the 1,2-indandiol, wherein the process comprises the steps of
(a) mixing in a solvent one equivalent of reactant, said reactant selected from ( 1S,2R)-indandiol or ( 1R,2R)-indandiol or mixture thereof, said solvent selected from an alkyl nitrile or aryl nitrile;
(b) adding to the mixture about two equivalents of an acid, said acid selected from a strong protic acid or a Lewis acid or an organic acid, and maintaining thereafter the temperature of the resulting mixture between about −70° C. and about 30° C. for a time period of between about 0.25 hours to about 6.0 hours; and
(c) adding excess water to effect hydrolysis, and stirring for a time period of between about 0.5 hour and about 8.0 hours, at a temperature of between about 25° C. and about 80° C., to give 1S-amino-2R-indanol.

Another embodiment is a regioselective process for synthesizing any enantiomer of cis-1-amino-2-indanol, or mixture of said enantiomers, from 1,2-indane diol, said process substantially retaining the stereochemical integrity of the carbon-oxygen bond at C-2 in the 1,2-indane diol, wherein the process comprises the steps of
(a) mixing one equivalent of reactant 1,2-indane diol in acetonitrile;
(b) adding dropwise to the mixture about two equivalents of concentrated sulfuric acid, and maintaining thereafter the temperature at about −70°–30° C. for about 30 minutes to one hour; and
(c) adding excess water to effect hydrolysis, and stirring, at a
temperature between about 25° C. and about 80° C., until
hydrolysis is complete, to give substantially cis-1-amino-2-indanol.

Another embodiment is a regioselective process, for synthesizing 1R-amino-2S-indanol from reactant (1R,2S)-indandiol or reactant (1S,2S)-indandiol or mixture of said reactants, said process substantially retaining the stereochemical integrity of the carbon-oxygen bond at C-2 in the 1,2-indandiol, wherein the process comprises the steps of
(a) mixing in acetonitrile one equivalent of reactant, said reactant selected from ( 1R,2S)-indandiol or ( 1S,2S) indandiol or mixture thereof;
(b) adding dropwise to the mixture about two equivalents of concentrated sulfuric acid, and maintaining thereafter the temperature at about −70°–30° C. for about 30 minutes to one hour; and
(c) adding excess water to effect hydrolysis, and stirring, at a
temperature between about 25° C. and about 80° C., until hydrolysis is complete, to give substantially 1R-amino-2S-indanol.

Another embodiment is a regioselective process, for synthesizing 1S-amino-2R-indanol from reactant (1S,2R)-indandiol or reactant (1R,2R)-indandiol or mixture of said reactants, said process substantially retaining the stereochemical integrity of the carbon-oxygen bond at C-2 in the 1,2-indandiol, wherein the process comprises the steps of
(a) mixing in acetonitrile one equivalent of reactant, said reactant selected from (1S,2R)-indandiol or (1R,2R)indandiol or mixture thereof;
(b) adding dropwise to the mixture about two equivalents of concentrated sulfuric acid, and maintaining thereafter the temperature at about −70°–30° C. for about 30 minutes to one hour; and
(c) adding excess water to effect hydrolysis, and stirring, at a temperature between about 25° C. and about 80° C., until hydrolysis is complete, to give substantially 1S-amino-2R-indanol.

B. 2-HALO-1-INDANOL PRECURSOR

This invention relates to a regioselective process for synthesizing any enantiomer of cis-1-amino-2-indanol, or mixture of said enantiomers, from 2-halo-1-indanol, said process substantially inverting the stereochemistry of the carbon at the 2-position of the indane core, wherein the process comprises the steps of
  (a) mixing one equivalent of 2-halo-1-indanol in a solvent, said solvent selected from an alkyl nitrile or aryl nitrile;
  (b) adding to the mixture at least about 1.5 equivalents of an acid, said acid selected from a strong protic acid or a Lewis acid or an organic acid, and maintaining thereafter the temperature of the resulting mixture between about −70° C. and about 30° C. for a time period of between about 0.25 hours to about 6.0 hours;
  (c) adding to the mixture strong base until the pH is greater than about 11; and
  (d) treating the product of Step c with a strong aqueous acid until the pH is less than about 3, to give cis-1-amino-2-indanol.

The present invention provides a process for the synthesis of cis-1-amino-2-indanol from 2-halo-1-indanol. In this particular application, 2-halo-1-indanol is readily synthesized by a variety of methods, both in racemic and optically pure form. The starting material, in any mixture of enantiomers including racemic and optically pure forms, is treated with a strong protic acid, such as sulfuric acid or $H_2SO_4\text{-}SO_3$, or Lewis acid such as boron trifluoride, or an organic acid such as p-toluenesulfonic acid, methanesulfonic acid, trifluoroacetic acid or trifluoromethanesulfonic acid. The reaction is carded out in a solvent comprising alkyl or aryl nitrile, e.g., acetonitrile, proprionitrile, or benzonitrile, at a temperature range of between about −70° C. to about +30° C., and an incubation period ranging from about 0.25 to about 6.0 hours.

In the second step, the solution is rendered alkaline by adding base. Adding a strong base until the pH is greater than about 11 is typically sufficient. Suitable strong bases include NaOH and KOH.

In a third step, a strong aqueous acid is added to lower the pH to less than about 3, to give the desired product cis-1-amino-2indanol. Examples of suitable acids include sulfuric acid, hydrochloric acid, or methanesulfonic acid. Isolation of this product as either its crystalline free base (i.e. amino-indanol) or as an amine salt derivative (e.g. a tartaric acid salt) can be accomplished directly from the reaction medium by pH adjustment to provide the desired form of the amino indanol intermediate.

One embodiment of the present invention is a regioselective process, for synthesizing 1S-amino-2R-indanol from 2S-bromo-1S-indanol, said process substantially inverting the stereochemistry of the carbon at the 2-position of the indane core, wherein the process comprises the steps of
  (a) mixing one equivalent of 2S-bromo-1S-indanol in a solvent, said solvent selected from an alkyl nitrile or aryl nitrile;
  (b) adding to the mixture about two equivalents of an acid, said acid selected from a strong protic acid or a Lewis acid or an organic acid, and maintaining thereafter the temperature of the resulting mixture between about −70° C. and about 30° C. for a time period of between about 0.25 hours to about 6.0 hours;
  (c) adding to the mixture strong base until the pH is greater than about 11; and
  (d) treating the product of Step c with a strong aqueous acid until the pH is less than about 3, to give substantially 1S-amino-2R-indanol.

Another embodiment is a regioselective process, for synthesizing 1R-amino-2S-indanol from 2R-bromo-1R-indanol, said process substantially inverting the stereochemistry of the carbon at the 2-position of the indane core, wherein the process comprises the steps of
  (a) mixing one equivalent of 2R-bromo-1R-indanol in a solvent, said solvent selected from an alkyl nitrile or aryl nitrile;
  (b) adding to the mixture about two equivalents of an acid, said acid selected from a strong protic acid or a Lewis acid or an organic acid, and maintaining thereafter the temperature of the resulting mixture between about −70° C. and about 30° C. for a time period of between about 0.25 hours to about 6.0 hours;
  (c) adding to the mixture strong base until the pH is greater than about 11; and
  (d) treating the product of Step c with a strong aqueous acid until the pH is less than about 3, to give substantially 1R-amino-2S-indanol.

Another embodiment is a regioselective process for synthesizing any enantiomer of cis-1-amino-2-indanol, or mixture of said enantiomers, from 2-halo-1-indanol, said process substantially inverting the stereochemistry of the carbon at the 2-position of the indane core, wherein the process comprises the steps of
  (a) mixing one equivalent of 2-halo-1-indanol in acetonitrile;
  (b) adding about 2 equivalents of sulfuric acid;
  (c) adding to the mixture aqueous potassium hydroxide until the pH is greater than 11; and
  (d) treating the product of Step c with sulfuric acid until the pH is less than 3, to give cis-1-amino-2-indanol.

Another embodiment is a regioselective process, for synthesizing 1S-amino-2R-indanol from 2S-bromo-1S-indanol, said process substantially inverting the stereochemistry of the carbon at the 2-position of the indane core, wherein the process comprises the steps of
  (a) mixing one equivalent of 2S-bromo-1S-indanol in acetonitrile;
  (b) adding about 2 equivalents of sulfuric acid;
  (c) adding to the mixture aqueous potassium hydroxide until the pH is greater than 11; and
  (d) treating the product of Step c with sulfuric acid until the pH is less than 3, to give substantially 1S-amino-2R-indanol.

Another embodiment is a regioselective process, for synthesizing 1R-amino-2S-indanol from 2R-bromo-1R-indanol, said process substantially inverting the stereochemistry of the carbon at the 2-position of the indane core, wherein the process comprises the steps of
  (a) mixing one equivalent of 2R-bromo-1R-indanol in acetonitrile;
  (b) adding about 2 equivalents of sulfuric acid;
  (c) adding to the mixture aqueous potassium hydroxide until the pH is greater than 11; and
  (d) treating the product of Step c with sulfuric acid until the pH is less than 3, to give substantially 1R-amino-2S-indanol.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention.

When any variable (e.g., aryl) occurs more than one time in any constituent, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl); As used herein, "aryl" is intended to mean phenyl (Ph) or naphthyl.

Representative experimental procedures utilizing the novel process are detailed below. These procedures are exemplary only and should not be construed as being limitations on the novel process of this invention.

EXAMPLE 1

Conversion of 1,2 indanol to cis-1-amino-2-indanol

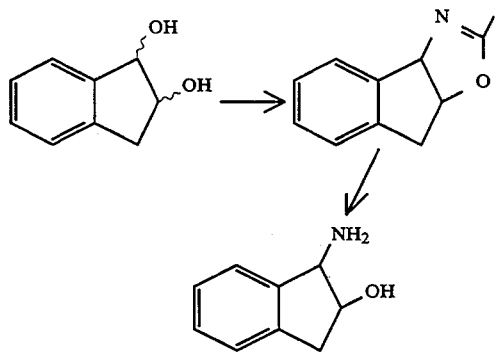

| Materials | Mol Wt | Grams or ml | Millimoles |
|---|---|---|---|
| 1,2 indane diol | 150 | 300 mg. | 2 |
| acetonitrile | 41 | 2.5 ml | 47.3 |
| water | 18 | 0.04 ml | 2 |
| sulfuric acid | 98 | 0.22 ml | 4 |
| 5N KOH | 57 | 1.6 ml | 8.0 |
| Dowex 50 × 4 (H+) | | 10 ml | |
| methanol (1 m NH3) | | 30 ml | |

To 300 mg indane diol dissolved in 3 ml of acetonitrile containing 0.04 ml water was added dropwise at 0°–10° C. a volume of 0.22 ml of concentrated $H_2SO_4$. After the addition was complete the ice bath was removed and the batch warmed to room temperature. After a 30 minute age the clear solution was sampled for Ic assay(?) (dilx 500). When all the glycol was consumed, the solution was treated further with water and heated to reflux on a steam bath to hydrolyze the oxazoline.

When Ic analysis showed hydrolysis complete, 1.6 ml 5NKOH was added to neutralize the sulfuric acid. Potassium sulfate was filtered from the solution.

The filtrate was assayed for cis amino indanol and contained 196 mg (66% of theory, which is also 75% corrected for unreacted starting material). The solution was passed over 10 ml of Dowex 50×4 (H+). The column spents were checked for product. All the amino indanol was adsorbed. After washing the resin with methanol, the product was eluted with a solution 1M in $NH_3$ (dry). The ammoniacal methanol was concentrated to remove the $NH_3$ and the final solution of amino-indanol ready for resolution was assayed. (175 mg, or 59% of theory when uncorrected for unreacted glycol).

EXAMPLE 2

Preparation of Indanol Reactants

Compounds (±)-trans-2-bromo-1-indanol were prepared by methods of S. M. Sutter et al., *J. Am. Chem. Soc.* 62, 3473 (1940); and D. R. Dalton et al., *J. C. S. Chem. Commun.* 591 (1966). Compounds (+)-trans-2-bromo-1-indanol and cis- and trans-1,2-indandiols were prepared by the methods of M. Imuta et al., *J. Org. Chem.*, 43, 4540 (1978).

EXAMPLE 3

Preparation of cis-1-amino-2-indanol from trans-2-bromo-1-indanol

Trans-2-bromo-1-indanol (10 g, 46.9 mmole diluted in 100 mL of acetonitrile containing 0.8 mL water) was cooled to −5° C. and concentrated sulfuric acid (5.2 mL) was added. The mixture was aged for 1 hr, then 5M aqueous potassium hydroxide was added to adjust the pH to 11. The reaction mixture was filtered, removing the potassium sulfate salts. The aqueous acetonitrile filtrate was adjusted to pH less than 2 with sulfuric acid and heated to 80°–100° C., removing acetonitrile by distillation to provide an aqueous solution of cis-1-amino-indanol. The solution was concentrated to a volume of 20 mL, then adjusted to pH 12.5 with potassium hydroxide. The product crystallizes, was filtered and dried in vacuo to provide cis-1-amino-2-indanol (4.25 g).

EXAMPLE 4

Preparation of cis-1S-amino-2R-indanol from cis-(1S,2R)-indandiol

Cis-(1S,2R)-indandiol (1 g) was dissolved in acetonitrile (10 mL), cooled to 0° C. and concentrated sulfuric acid (1.0 mL) was added. The mixture was aged for 40 minutes with warming to 20° C. Water (0.8 mL) was added and the mixture was heated to reflux. Aqueous 5M potassium hydroxide (1.6 mL) was added to adjust the pH to more than 11 and the resulting solid (potassium sulfate) removed by filtration to provide an aqueous solution of the cis-1S-amino-2R-indanol (0.79 g, 66% yield).

EXAMPLE 5

Preparation of cis-1-amino-2-indanol from trans-1,2-indandiol

Trans-1,2-indandiol (1.5 g) was dissolved in acetonitrile (25 mL) cooled to 0° C., and concentrated sulfuric acid (1.1 mL) was added. The mixture was gradually warmed to 20° C. and aged to 3 hours. Water (2 mL) was added and the mixture heated to reflux. Concentrated aqueous sodium hydroxide was added to adjust the pH to 12. The resulting solid was removed by filtration to provide an aqueous acetonitrile solution of cis-1-amino-2-indanol (1.02 g, 63% yield).

EXAMPLE 6

Preparation of cis-1-amino-2-indanol from cis-1,2-indandiol

Cis-1,2-indandiol (1.0 g) was dissolved in acetonitrile (20 mL), cooled to −40° C., and fuming sulfuric acid (21% $SO_3$, 0.8 mL) was added. The mixture was aged for 1 hour with gradual warming to 0° C. Water was added and the mixture heated to 80° C. for 1 hour to provide an aqueous solution of cis-1-amino-2-indanol.

EXAMPLE 7

Preparation of Amide 1

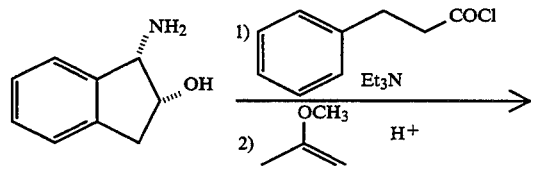

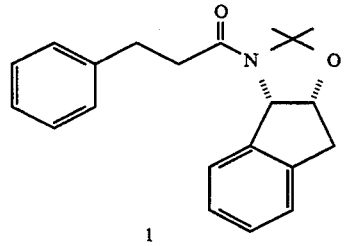

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4/K_2HPO_4$), 1.0 mL/min., injection volume=20 mL, detection=200 nm, sample preparation=500 X dilution. Approximate retention times:

| retention time (min.) | identity |
|---|---|
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area% by HPLC), $^1$H NMR (300.13 MHz, $CDCl_3$, major rotamer) $\delta$7.36–7.14 (m, 9H), 5.03 (d, J=4.4, 1H), 4.66 (m, 1H) 3.15 (m, 2H), 3.06 (br s, 2H), 2.97 (m, 2H), 1.62 (s, 3H), 1.37 (s, 3H); $^{13}$C NMR (75.5 MHz, $CDCl_3$, major rotamer) $\delta_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1. Anal. Calcd for $C_{21}H_{23}NO_2$: C, 78.47; H, 7.21; N, 4.36. Found: C, 78.65; H, 7.24; N, 4.40.

EXAMPLE 8

Preparation of Epoxide 3 Tosylate Method

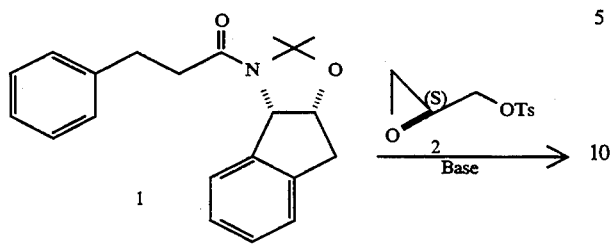

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide (LiN[(CH$_3$)$_3$Si]$_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection=254 nm, sample preparation=100×dilution. Approximate retention times:

| retention time (min.) | identity |
| --- | --- |
| 5.5 | amide 1 |
| 6.5 | glycidyl tosylate 2 |
| 13.5 | epoxide 3 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $^{13}$C NMR (300 MHz, CDCl$_3$) δ171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 9

Preparation of penultimate 6

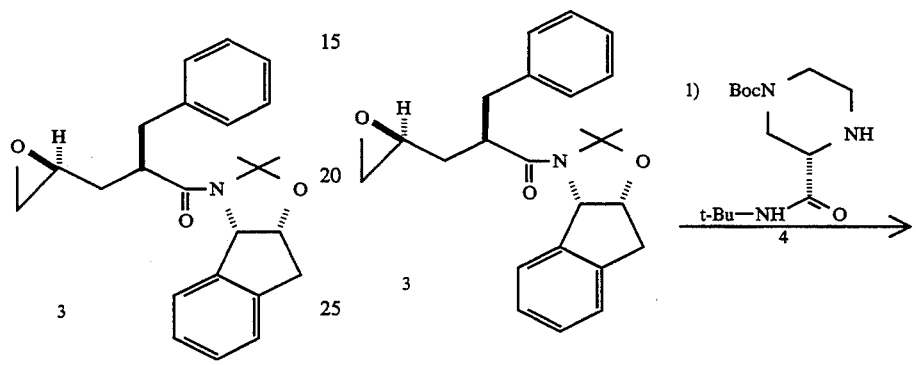

A slurry of the 2(S)-t-butylcarboxamide-4-N-Boc-piperazine 4 (1950 g, 6.83 mol, >99.5% ee) (ee=enantiomeric excess) and the epoxide 3 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°-85° C.). After 40 min, a homogeneous solution was obtained. The mixture was heated at reflux for 28 h.

The internal temperature during reflux was 84°-85° C. Progress of the reaction was monitored by HPLC analysis: 25 cm Dupont C8-RX column, 60:40 acetonitrile/10 mM (KH$_2$PO$_4$/K$_2$HPO$_4$), 1.0 mL/min., detection=220 nm, sample preparation=2 μL, reaction mixture diluted to 1 mL in acetonitrile. Approximate retention times:

| retention time (min.) | identity |
|---|---|
| 4.8 | piperazine 4 |
| 8.9 | epoxide 3 |
| 15.2 | coupled product 5 |

After 28 h, the remaining epoxide 3 and coupled product 5 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min.) | identity |
|---|---|
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF= 1.8 mg/mL). The HPLC assay yield of 6 in ethyl acetate was 86.5%. The penultimate compound 6 in DMF was directly used in the next step without further purification. For isolated 6: $^{13}$C NMR (75.4 MHz, CDCl$_3$) δ 175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 10

Preparation of monohydrate of Compound J

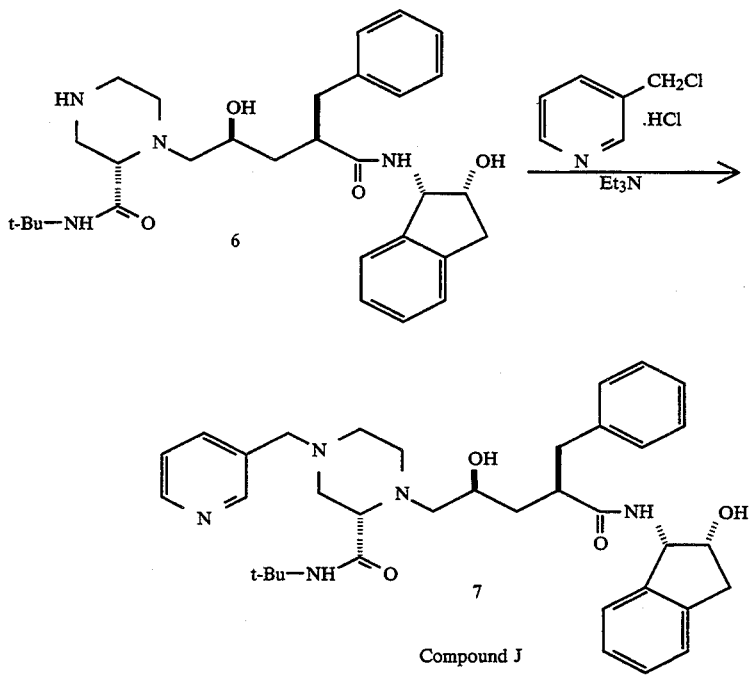

The solution of 6 in DMF (10.5 L, KF=10 mg/mL) from the previous step was charged with 8 L of sieve dried DMF (KF.<30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min.) | identity |
|---|---|
| 2.7 | DMF |
| 4.2 | 3-picolyl chloride |
| 4.8 | Compound J |
| 9.1 | penultimate 6 |

The mixture was aged at 68° C. until the residual penultimate compound 6 was <0.3 area % by HPLC analysis.

The mixture was stirred at 68° C. for 4 h, then cooled to 25° C. and partitioned with ethyl acetate (80 L) and a mixture of 24 L of saturated aqueous NaHCO$_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 11

Pyrazine-2-tert-butyl carboxamide 9

| | |
|---|---|
| 2-Pyrazinecarboxylic acid (8) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 8 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 8 remained.

The assay for completion of the acid chloride formation is important because incomplete reaction leads to formation of a bis-tertbutyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atatmospheric pressure for several days.

Evaporation of an aliquot gave a tan solid m.p 87°–88° C. $^{13}C$ NMR (75 MHz, $CDCl_3$, ppm) 161.8, 146.8, 145.0, 143.8, 142.1, 51.0, 28.5.

EXAMPLE 12 rac-2-tert-Butyl-carboxamide-piperazine 10

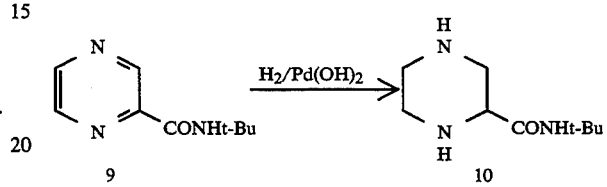

Materials

Pyrazine-2-tert-butylcarboxamide 9 2.4 kg (13.4 mol) in 1-Propanol solution 12 L 20% $Pd(OH)_2/C$ 16 wt. % water 144 g.

The pyrazine-2-tert-butylcarboxamide 9/1-propanol solution was placed into the 5 gal autoclave. The catalyst was added and the mixture was hydrogenated at 65° C. at 40 psi (3 atm) of $H_2$.

After 24 h. the reaction had taken up the theoretical amount of hydrogen and GC indicated <1% of 9. The mixture was cooled, purged with $N_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C/min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 133 g/L.

Evaporation of an aliquot gave 10 as a white solid m.p. 150°–151° C.; $^{13}C$ NMR (75 MHz, $D_2O$, ppm) 173.5, 59.8, 52.0, 48.7, 45.0, 44.8, 28.7.

EXAMPLE 13

(S)-2-tert-Butyl-carboxamide-piperazine bis (S)-Camphorsulfonic acid salt (S)-11

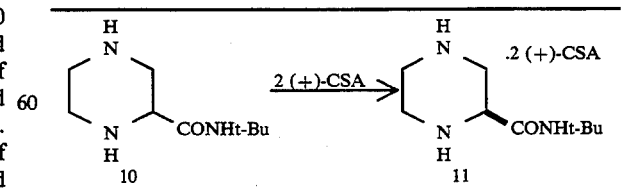

Materials

| | |
|---|---|
| rac-2-tert-Butyl-carboxamide-piperazine 10 | 4.10 kg (22.12 mol) |
| in 1-Propanol Solution | in 25.5 Kg solvent |
| (S)-(+)-10-Camphorsulfonic acid | 10.0 Kg (43.2 mol) |

-continued

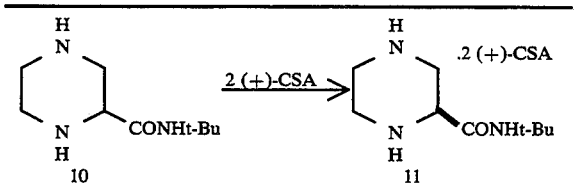

| Materials | |
|---|---|
| 1-Propanol | 12 L |
| Acetonitrile | 39 L |
| Water | 2.4 L |

The solution of amine 10 in 1-propanol was charged to a L flask with an attached batch concentrator. The solution was concentrated at 10 mbar and a temperature <25° C. to a volume of ca 12 L.

At this point the product had precipitated from the solution, s but went back into a solution when the mixture was heated to 50° C.

Analysis of a homogeneous aliquot indicated that the concentration of 10 was 341 g/L. The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 10:2.5 min.

Acetonitrile (39 L) and water (2.4 L) were added to give a clear, slightly brown solution.

Determination of the water content by KF titration and $CH_3CN/1$-propanol ratio by $^1H$ NMR integration showed that the $CH_3CN/1$-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN/1$-propanol/$H_2O$ 26/8/1.6 solvent mixture. It was dried at 35° C. in the vacuum oven with $N_2$ bleed to give 5.6 Kg (39%) of 11 as a white crystalline solid m.p 288°–290° C. (with decomp.) $[\alpha]D^{25}=18.9°$ (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 14

(S)-2-tert-Butylcarboxamide-4-tert-butoxycarbonyl-piperazine 4 from salt 11

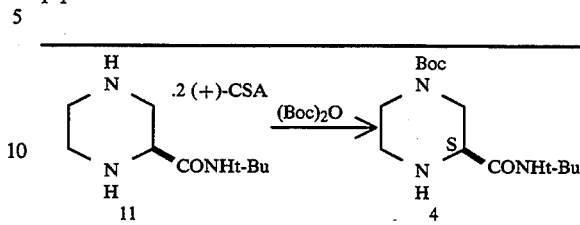

| Materials | |
|---|---|
| (S)-2-tert-Butyl-carboxamide-piperazine Bis (S)-(+)-CSA salt 11, 95% ee | 5.54 Kg (8.53 mol) |
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 11 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC:25 cm Dupont Zorbax RXC8 column with 1 mL/min flow and detection at 228 nm, isocratic (50/50) $CH_3CN/0.1M$ $KH_2PO_4$ adjusted to pH=6.8 with NaOH. Retention time of 4=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L DI water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area by HPLC, R-isomer below level of detection) of 4 as a slightly tan powder. $[\alpha9 D^{25}=22.0°$ (c=0.20, MeOH), m.p 107° C.; $^{13}C$ NMR (75 MHz, $CDCl_3$, ppm) 170.1, 154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A regioselective process for synthesizing any enantiomer of cis-1-amino-2-indanol, or mixture of said enantiomers, from 2-halo-1-indanol, said process substantially inverting the stereochemistry of the carbon at the 2-position of the indane core, wherein the process comprises the steps of
    (a) mixing one equivalent of 2-halo-1-indanol in a solvent, said solvent selected from an alkyl nitrile or aryl nitrile;
    (b) adding to the mixture at least about 1.5 equivalents of an acid, said acid selected from a strong protic acid or a Lewis acid or an organic acid, and maintaining thereafter the temperature of the resulting mixture between about $-70°$ C. and about $30°$ C. for a time period of between about 0.25 hours to about 6.0 hours;
    (c) adding to the mixture strong base until the pH is greater than about 11; and
    (d) treating the product of Step c with a strong aqueous acid until the pH is less than about 3, to give cis-1-amino-2-indanol.

2. A regioselective process, according to claim 1, for synthesizing 1S-amino-2R-indanol from 2S-bromo-1S-indanol, said process substantially inverting the stereochemistry of the carbon at the 2-position of the indane core, wherein the process comprises the steps of
    (a) mixing one equivalent of 2S-bromo-1S-indanol in a solvent, said solvent selected from an alkyl nitrile or aryl nitrile;
    (b) adding to the mixture about two equivalents of an acid, said acid selected from a strong protic acid or a Lewis acid or an organic acid, and maintaining thereafter the temperature of the resulting mixture between about $-70°$ C. and about $30°$ C. for a time period of between about 0.25 hours to about 6.0 hours;
    (c) adding to the mixture strong base until the pH is greater than about 11; and
    (d) treating the product of Step c with a strong aqueous acid until the pH is less than about 3, to give substantially 1S-amino-2R-indanol.

3. A regioselective process, according to claim 1, for synthesizing 1R-amino-2S-indanol from 2R-bromo-1R-indanol, said process substantially inverting the stereochemistry of the carbon at the 2-position of the indane core, wherein the process comprises the steps of
    (a) mixing one equivalent of 2R-bromo-1R-indanol in a solvent in water, said solvent selected from an alkyl nitrile or aryl nitrile;
    (b) adding to the mixture about two equivalents of an acid, said acid selected from a strong protic acid or a Lewis acid or an organic acid, and maintaining thereafter the temperature of the resulting mixture between about $-70°$ C. and about $30°$ C. for a time period of between about 0.25 hours to about 6.0 hours;
    (c) adding to the mixture strong base until the pH is greater than about 11; and
    (d) treating the product of Step c with a strong aqueous acid until the pH is less than about 3, to give substantially 1R-amino-2S-indanol.

4. A regioselective process for synthesizing any enantiomer of cis-1-amino-2-indanol, or mixture of said enantiomers, from 2-halo-1-indanol, said process substantially inverting the stereochemistry of the carbon at the 2-position of the indane core, wherein the process comprises the steps of
    (a) mixing one equivalent of 2-halo-1-indanol in acetonitrile;
    (b) adding about 2 equivalents of sulfuric acid;
    (c) adding to the mixture aqueous potassium hydroxide until the pH is greater than 11; and
    (d) treating the product of Step c with sulfuric acid until the pH is less than 3, to give cis-1-amino-2-indanol.

5. A regioselective process, according to claim 4, for synthesizing 1S-amino-2R-indanol from 2S-bromo-1S-indanol, said process substantially inverting the stereochemistry of the carbon at the 2-position of the indane core, wherein the process comprises the steps of
    (a) mixing one equivalent of 2S-bromo-1S-indanol in acetonitrile;
    (b) adding about two equivalents of sulfuric acid;
    (c) adding to the mixture aqueous potassium hydroxide until the pH is greater than 11; and
    (d) treating the product of Step c with sulfuric acid until the pH is less than 3, to give substantially 1S-amino-2R-indanol.

6. A regioselective process, according to claim 4, for synthesizing 1R-amino-2S-indanol from 2R-bromo-1R-indanol, said process substantially inverting the stereochemistry of the carbon at the 2-position of the indane core, wherein the process comprises the steps of
    (a) mixing one equivalent of 2R-bromo-1R-indanol in acetonitrile;
    (b) adding about two equivalents of sulfuric acid;
    (c) adding to the mixture aqueous potassium hydroxide until the pH is greater than 11; and
    (d) treating the product of Step c with sulfuric acid until the pH is less than 3, to give substantially 1R-amino-2S-indanol.

* * * * *